(12) United States Patent
Bradner et al.

(10) Patent No.: US 9,535,067 B2
(45) Date of Patent: Jan. 3, 2017

(54) DOT1L PROBES

(71) Applicant: DANA-FARBER CANCER INSTITUTE, INC., Boston, MA (US)

(72) Inventors: James E. Bradner, Weston, MA (US); Alexander Federation, Boston, MA (US); Jun Qi, Sharon, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/904,572

(22) PCT Filed: Jul. 28, 2014

(86) PCT No.: PCT/US2014/048375
§ 371 (c)(1),
(2) Date: Jan. 12, 2016

(87) PCT Pub. No.: WO2015/017311
PCT Pub. Date: Feb. 5, 2015

(65) Prior Publication Data
US 2016/0146817 A1    May 26, 2016

Related U.S. Application Data

(60) Provisional application No. 61/859,654, filed on Jul. 29, 2013.

(51) Int. Cl.
| | | |
|---|---|---|
| *A01N 43/90* | (2006.01) | |
| *A61K 31/52* | (2006.01) | |
| *G01N 33/573* | (2006.01) | |
| *A61K 31/7076* | (2006.01) | |
| *C07H 19/16* | (2006.01) | |
| *G01N 33/58* | (2006.01) | |

(52) U.S. Cl.
CPC ......... *G01N 33/573* (2013.01); *A61K 31/7076* (2013.01); *C07H 19/16* (2013.01); *G01N 33/582* (2013.01); *G01N 2333/91017* (2013.01); *G01N 2500/02* (2013.01)

(58) Field of Classification Search
None
See application file for complete search history.

(56) References Cited

U.S. PATENT DOCUMENTS

| 2012/0142625 A1 | 6/2012 | Olhava et al. |
| 2014/0051654 A1 | 2/2014 | Olhava et al. |
| 2014/0100184 A1 | 4/2014 | Song et al. |
| 2016/0060269 A1 | 3/2016 | Bradner et al. |

FOREIGN PATENT DOCUMENTS

| WO | 2012/082436 | 6/2012 |
| WO | 2013/055397 | 4/2013 |
| WO | WO 2015/017311 | 2/2015 |

OTHER PUBLICATIONS

International Search Report and Written Opinion issued in PCT/US2014/048375 (Dec. 23, 2014).
U.S. Non-Final Office Action for U.S. Appl. No. 14/838,142 dated Jun. 28, 2016, 51 pages.
McLean et al. The emerging roles of DOT1L in leukemia and normal development. Leukemia (2014) 28, 2131-2138.

*Primary Examiner* — Jeffrey H Murray
(74) *Attorney, Agent, or Firm* — Fish & Richardson P.C.

(57) ABSTRACT

The present invention relates to compound that bind Histone H3-lysine79 (H3K79) methyl transferase (DOT1L). The disclosed compounds are useful as for assessing the activity of DOT1L and for identifying inhibitors of DOT1L. Described herein are probes useful for both assessing the activity of DOT1L and identifying inhibitors of DOT1L. These probes can be used in various assays, including Amplified Luminescent Proximity Homogeneous Assays ("ALPHA" assays), Differential Scanning Fluorimetry (DFS) Assay, and Fluorescence Polarization (FP) assays used for high-throughput screening (HTS) for small molecule drug discovery. The compounds can also be used as a pull down agent for target identification.

21 Claims, 1 Drawing Sheet

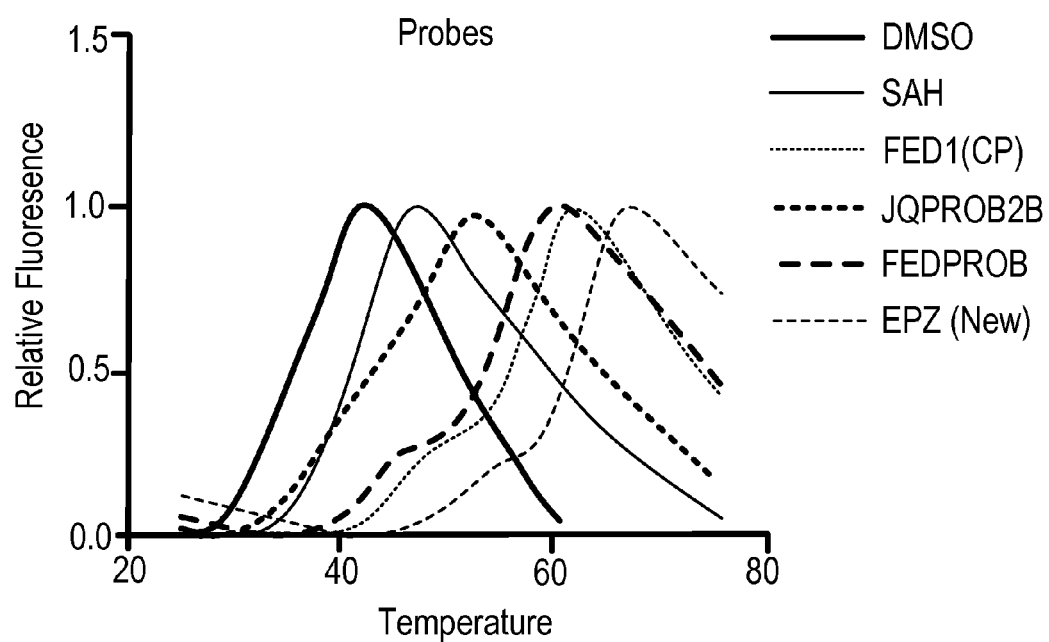

DOT1L PROBES

CROSS REFERENCE TO RELATED APPLICATIONS

This is a United States National Phase Application under 35 U.S.C. §371 of International Patent Application No. PCT/US2014/048375, filed Jul. 28, 2014, which claims the benefit of U.S. Provisional Application No. 61/859,654, filed on Jul. 29, 2013, the disclosures of each of which are incorporated herein by reference in their entireties.

TECHNICAL FIELD

This invention relates to compounds (e.g. probes) that bind to Histone H3-lysine79 (H3K79) methyl transferase ("DOT1-Like Histone H3K79 Methyltransferase" or "DOT1L"), and more particularly to probes useful for purposes such as assessing the activity of DOT1L and identifying inhibitors of DOT1L

BACKGROUND

DOT1L plays important roles in normal cell differentiation as well as initiation of acute leukemia. DOT1L specifically catalyzes methylation of the histone H3-lysine79 (H3K79) residue located in the nucleosome core structure. DOT1L appears to be necessary and sufficient for the initiation and maintenance of leukemia with MLL (mixed lineage leukemia) gene translocations. DOT1L catalyzes an SN2 reaction of the H3K79 ε-NH2 of the substrate nucleosome with the methyl group of S-(5'-adenosyl)-L-methionine (SAM), the enzyme co-factor.

SUMMARY

Described herein are probes useful for both assessing the activity of DOT1L and identifying inhibitors of DOT1L. These probes can be used in various assays, including Amplified Luminescent Proximity Homogeneous Assays ("ALPHA" assays), Differential Scanning Fluorimetry (DFS) Assay, and Fluorescence Polarization (FP) assays used for high-throughput screening (HTS) for small molecule drug discovery. The compounds can also be used as a pull down agent for target identification. The compounds bind DOT1L with high affinity and are adaptable in that various fluorescence reagents can be attached to a variety of positions as can other markers, detectable tags, and affinity reagents. Importantly, by modifying the groups present at certain positions, the affinity of the compounds can be tuned for different purposes.

In one aspect, the disclosure features probe compounds of formula (I):

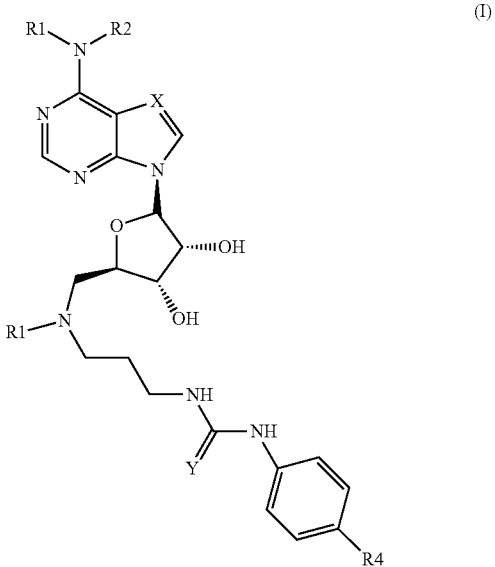

wherein:
X is N or C—R5;
Y is O or S;
R1 is hydrogen or $C_{1-3}$ alkyl;
R2 is hydrogen, $C_{1-3}$ alkyl, or R6;
R3 is hydrogen, $C_{1-6}$ alkyl, or R6;
R4 is $C_{1-8}$ alkyl, or N(R6)(R7)
provided that one of R2, R3, and R4 is, or includes, R6;
R5 is hydrogen, halo, $C_{1-6}$ alkyl, or $C_{1-6}$ haloalkyl; and
R6 is Z—R8;
Z is a divalent group consisting of any 1, 2, 3, 4, or 5 of the following independently selected moieties:
  (i) $C_{1-30}$ alkylene;
  (ii) a heteroalkylene that spans from 3-20 atoms in length wherein from 1-8 of the atoms in the span are heteroatomic groups that are each independently selected from N, NH, N—$C_{1-6}$ alkyl, O, and S, provided that there is at least one carbon atom between the occurrence of any two heteroatomic groups;
  (iii) a polyheteroalkylene chain that spans from 21-100 atoms in length wherein from 1-50 of the atoms in the span are heteroatomic groups that are each independently selected from N, NH, N—$C_{1-6}$ alkyl, O, and S, provided that there is at least one carbon atom between the occurrence of any two heteroatomic groups;
  (iv) a $C_{2-30}$ alkenylene chain,
  (v) —OC(=O)—, —C(=O)O—, —NHC(=O)—, —C(=O)NH—, —NHC(=O)NH—, —NHC(=S)NH—, —OC(=O)NH—, and —NHC(=O)O—;
R7 is hydrogen or $C_{1-3}$ alkyl; and
R8 is an affinity tag or a fluorescent label.

In some embodiments: R2 is R6; R3 is R6; R4 is N(R6)(R7); R7 is hydrogen; R8 is an affinity tag; R8 is a protein affinity tag; R8 has an affinity for streptavidin: R8 has formula (II):

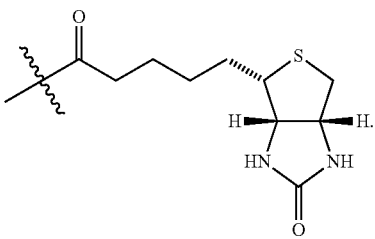

In some embodiments, R8 is a fluorescent label (e.g., R8 is FITC).

In some embodiments, Z is a divalent group consisting of one or two independently selected $C_{1-30}$ alkylenes; a heteroalkylene or polyheteroalkylene; and one of the following: —NHC(=O)—, —C(=O)NH—, or —NHC(=S)NH—; Z is a divalent group consisting of one or two independently selected $C_{1-30}$ alkylenes; a heteroalkylene; and —NHC(=O)— or —C(=O)NH— (e.g., when R8 is an affinity tag, e.g., having formula (II)); Z is a divalent group consisting of one or two independently selected $C_{1-30}$ alkylenes; a polyheteroalkylene; and —NHC(=O)— or —C(=O)NH— (e.g., when R8 is an affinity tag, e.g., having formula (II)); and Z is a divalent group consisting of one or two independently selected $C_{1-30}$ alkylenes and —NHC(=S)NH— (e.g., when R8 is a fluorescent label, e.g., FITC).

In some embodiments, the polyheteroalkylene is (PEG)n, wherein PEG represents a polyethylene glycol, and n is an integer from 2-27; R3 is $C_{1-6}$ alkyl; R3 is isopropyl; R4 is $C_{1-8}$ alkyl; R4 is methyl or tert-butyl; R2 is hydrogen; R4 is $C_{1-8}$ alkyl; R4 is methyl or tert-butyl; R2 is hydrogen; R3 is $C_{1-6}$ alkyl; R3 is isopropyl; X is N; and Y is O.

In one aspect, the disclosure relates to biotinylated compounds (e.g., biotinylated probes) of formula (Ia), (Ib), (Ic) or (Id):

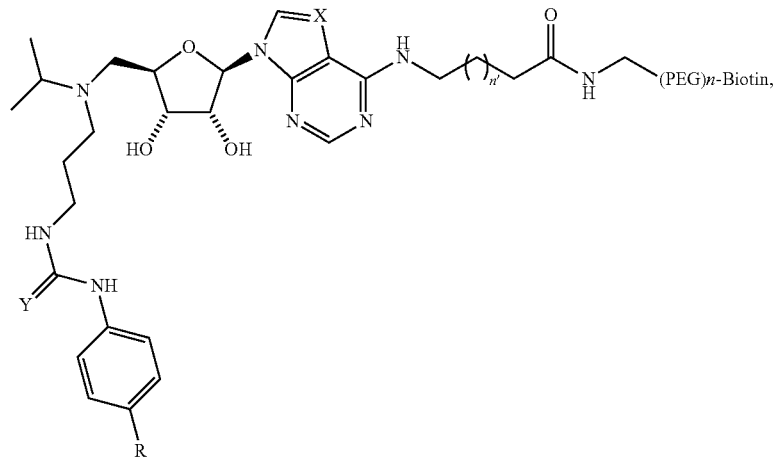

(Ia)

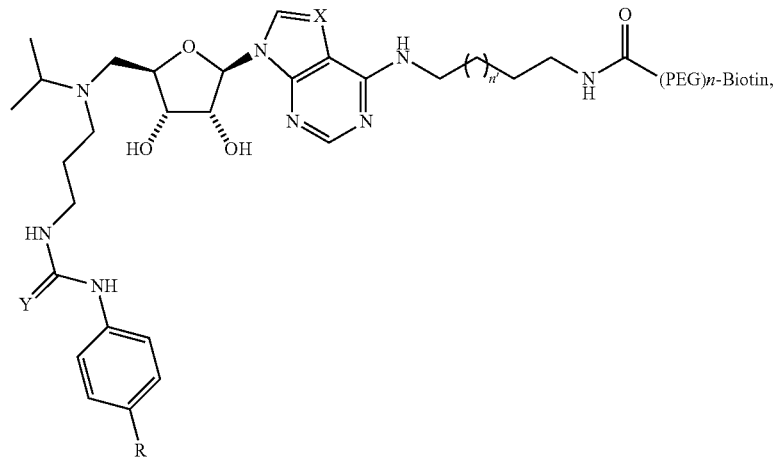

(1b)

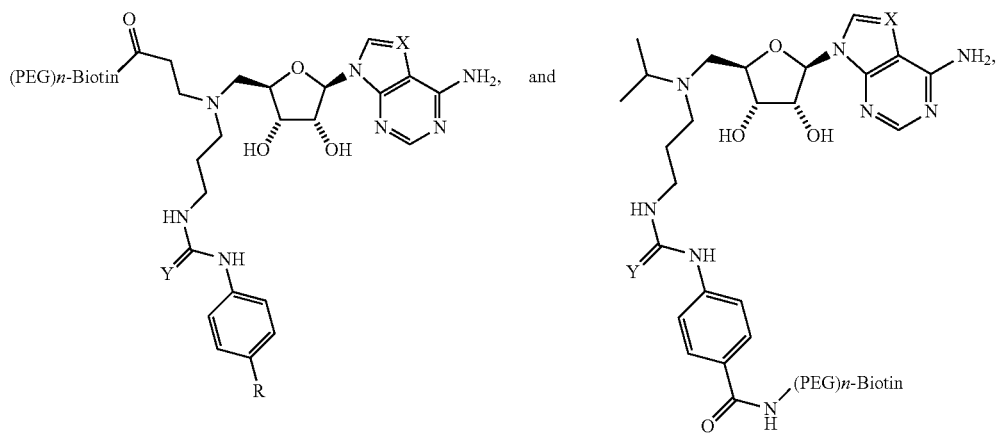
wherein:
X is N, CH, C—Cl, C—CH₃, or C—CF₃;
Y is O or S;
R is t-butyl or methyl;
n is 2-27; and
n' is 0-10.
In some embodiments, the disclosure relates to fluorescence tagged compounds of formula Ie or If:
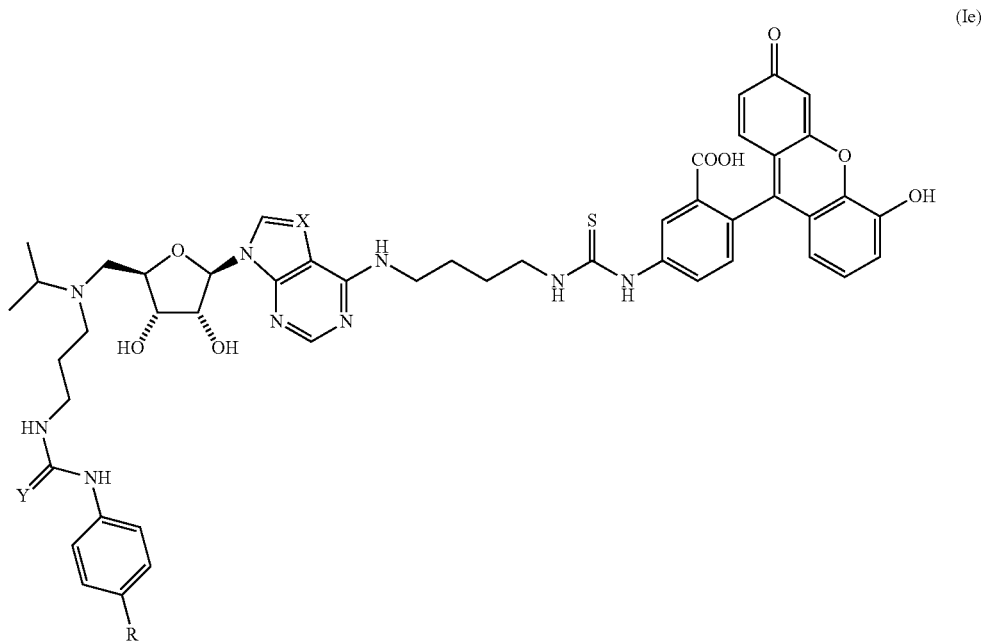

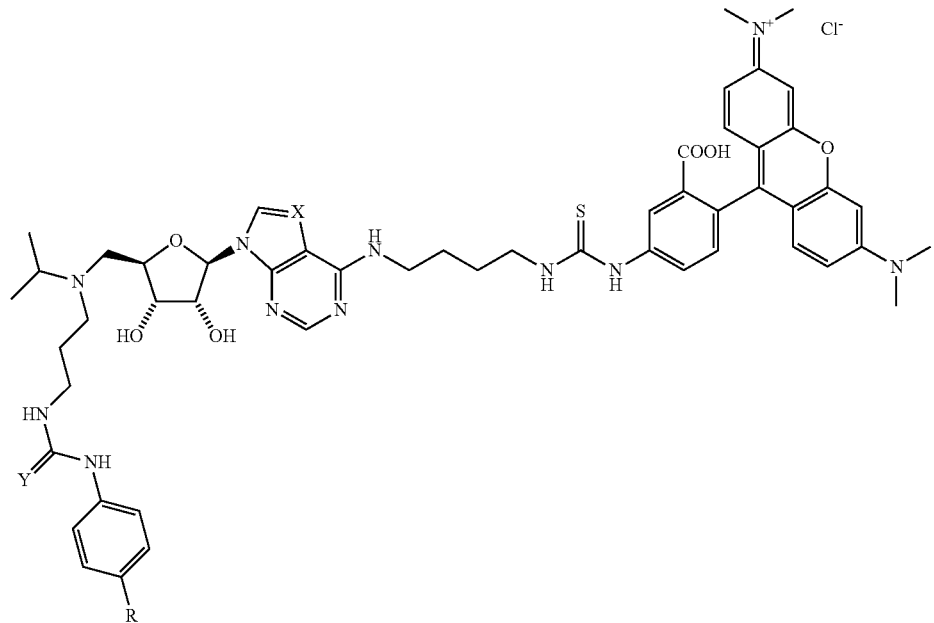
wherein,
X is N, CH, C—Cl, C—CH₃, or C—CF3;
Y is O or S; and
R is t-butyl or methyl.
In some embodiments, the disclosure relates to a fluorescence tagged compounds of formula (Ig):
(Ig)
As described herein, the compound of formula (Ig) is also referred to as "FED-FITC,"
In some embodiments: the compound is selected from the group consisting of formula (III), formula (IV) and formula (V):

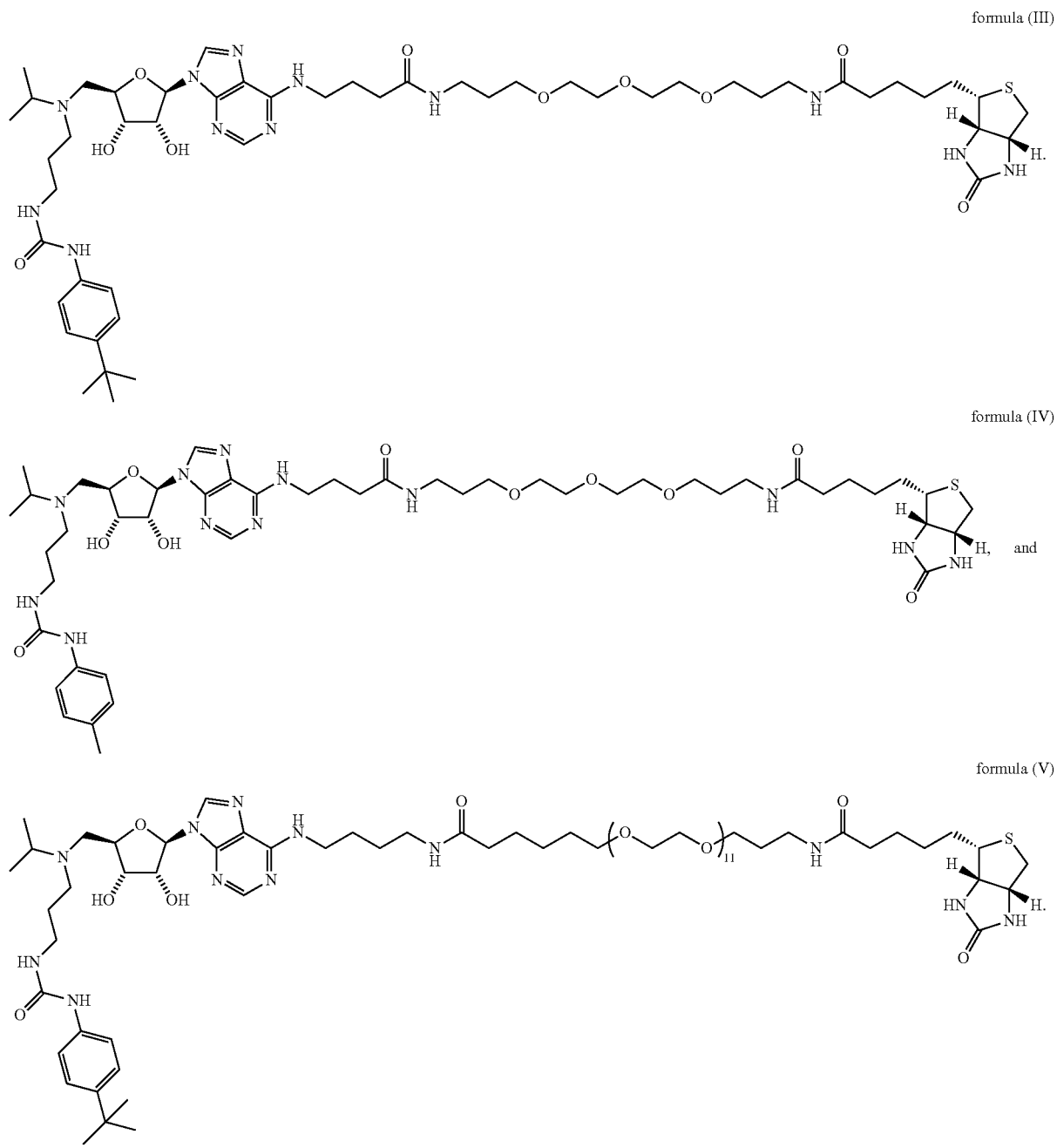

As described herein, the compound of formula (III) is also referred to as "JQPROB2B," the compound of formula (IV) is also referred to as 'JQPROB2B-Me,' and the compound of formula (V) is also referred to as "JQPROB11."

In some aspects, the probe is covalently or non-covalently bound to a solid support (e.g., a bead). In some embodiments: the bead emits singlet oxygen upon excitation by light; the bead is coated with a protein (e.g., streptavidin); or the protein is bound to the compound through association with R8; and R8 has formula (II).

As used herein, the term "alkyl" is defined to include saturated aliphatic hydrocarbons including straight chains and branched chains. Preferably, the alkyl group has 1 to 6 carbon atoms. For example, as used herein, the term "$C_{1-6}$ alkyl," as well as the alkyl moieties of other groups referred to herein (e.g., $C_{1-6}$ haloalkyl), refers to linear or branched radicals of 1 to 6 carbon atoms (e.g., methyl, ethyl, n-propyl, isopropyl, n-butyl, isobutyl, sec-butyl, tert-butyl, n-pentyl, isopentyl, neopentyl, and n-hexyl), optionally substituted by 1 to 5 suitable substituents. Alkyl groups may be substituted or unsubstituted. In particular, unless otherwise specified, alkyl groups may be substituted by one or more halo groups, up to the total number of hydrogen atoms present on the alkyl moiety. Thus, $C_{1-6}$ alkyl may include includes halogenated alkyl groups, Whenever a numerical range is used in this application, for example when 1 to 6 is used in the definition of "alkyl", it means that the alkyl group may contain 1 carbon atom, 2 carbon atoms, 3 carbon atoms, etc. up to and including 6 carbon atoms.

Alkyl groups described herein as optionally substituted by may be substituted by one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, preferably from 1 to 4 optional substituents, or more preferably from 1 to 3 optional substituents.

As used herein, the term "heteroalkyl," by itself or in combination with another term, refers to an alkylalkyl group as described above, wherein one or more non-contiguous carbon atoms of the alkylene chain are replaced by heteroatomic groups that are each independently selected from N, N(R), O, and S, where R is H or C1-6 alkyl, provided that there is at least one carbon atom between the occurrence of any two heteroatomic groups.

As used herein, the term "halo" or "halogen" group is defined to include fluorine, chlorine, bromine or iodine.

As used herein, the term "alkylene," by itself of as part of another term, refers to a saturated, branched or straight chain or cyclic hydrocarbon radical of the stated number of carbon atoms, typically 1-30 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethylene —$CH_2CH_2$—), 1,3-propylene (—$CH_2CH_2CH_2$—), 1,4-butylene (—$CH_2CH_2CH_2CH_2$—), and the like.

The term "heteroalkylene" refers to an alkylene group as described above, wherein one or more non-contiguous carbon atoms of the alkylene chain are replaced by heteroatomic groups that are each independently selected from N, N(R), O, and S, where R is H or $C_{1-6}$ alkyl, provided that there is at least one carbon atom between the occurrence of any two heteroatomic groups.

The term "affinity tag" as used herein refers moiety that is used to facilitate purification of another molecule (e.g., a probe, protein or polypeptide). Affinity tags may be attached the probe molecule by any suitable method. Affinity tags generally fall into three categories: a) peptide sequences that bind to small molecules; b) fusion proteins that bind to small molecules; and c) peptide tags or fusion proteins that bind to antibodies. An affinity tag may also be a small molecule that has a convenient binding partner. As one example, an affinity tag such as biotin may be chemically coupled, for instance covalently, to a target protein or peptide to facilitate the binding of the target to streptavidin. Affinity tags include, for example, metal binding tags such as histidine tags, GST (in glutathione/GST binding), streptavidin (in biotin/streptavidin binding). Other affinity tags include Myc or Max in a Myc/Max pair, or polyamino acids, such as polyhistidines.

As used herein, the terms "fluorescence label" and "fluorophore" used interchangeably and refer to any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals.

Representative fluorescence labels include but are not limited to fluoroscein 5-isothiocyanate (FITC), Alexa Fluor® 350, Dansyl Chloride (DNS-C1), 5-(iodoacetamida) fluoroscein (5-IAF); tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-C1), ethidium bromide, Lucifer Yellow, 5-carboxyrhodamine 6G hydrochloride, Lissamine rhodamine B sulfonyl chloride, Texas Red™, sulfonyl chloride, BODIPY™, naphthalamine sulfonic acids including but not limited to 1-anilinonaphthalene-8-sulfonic acid (ANS) and 6-(p-toluidinyl)naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-C3-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a graph demonstrating the results of a DFS Assay (DMSO, SAH (S-adenosylhomocysteine), EPZ (EPZ004777 reported by Epizyme), JQPROB2B (e.g., a compound of formula (III)), FED1(CP), and FEDPROB) are shown)

DETAILED DESCRIPTION

The inventors have designed and identified compounds (e.g., formula (I)) that bind to DOT1L with high affinity. Thus, inventors have designed and identified compounds useful as probes for both assessing the activity and identifying inhibitors of DOT1L.

All of the compounds of formula (I) can be prepared by conventional routes such as by the procedures described in the general methods presented below, or by similar methods thereto. The present invention also encompasses these processes for preparing the compounds of formula (I), in addition to any novel intermediates used therein.

According to a first process, compounds of formula (I) (e.g., compounds of formula (Ic)) may be prepared as illustrated by Scheme 1.

Scheme 1
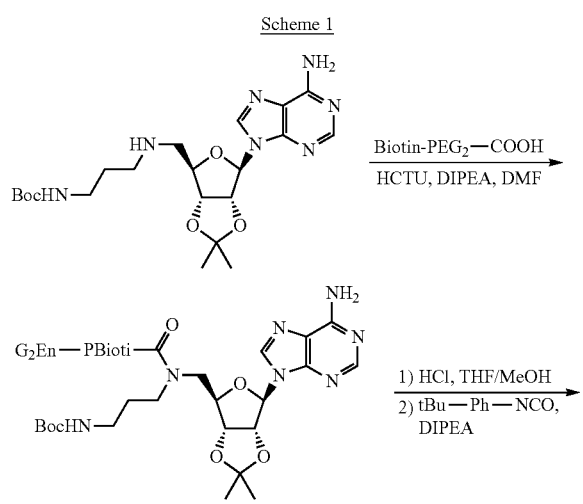
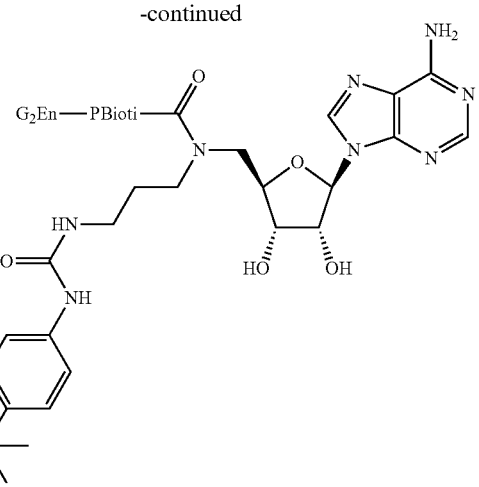
According to a second process, compounds of formula (I) (e.g., compounds of formula (Ib)) may be prepared as illustrated by Scheme 2.
Scheme 2
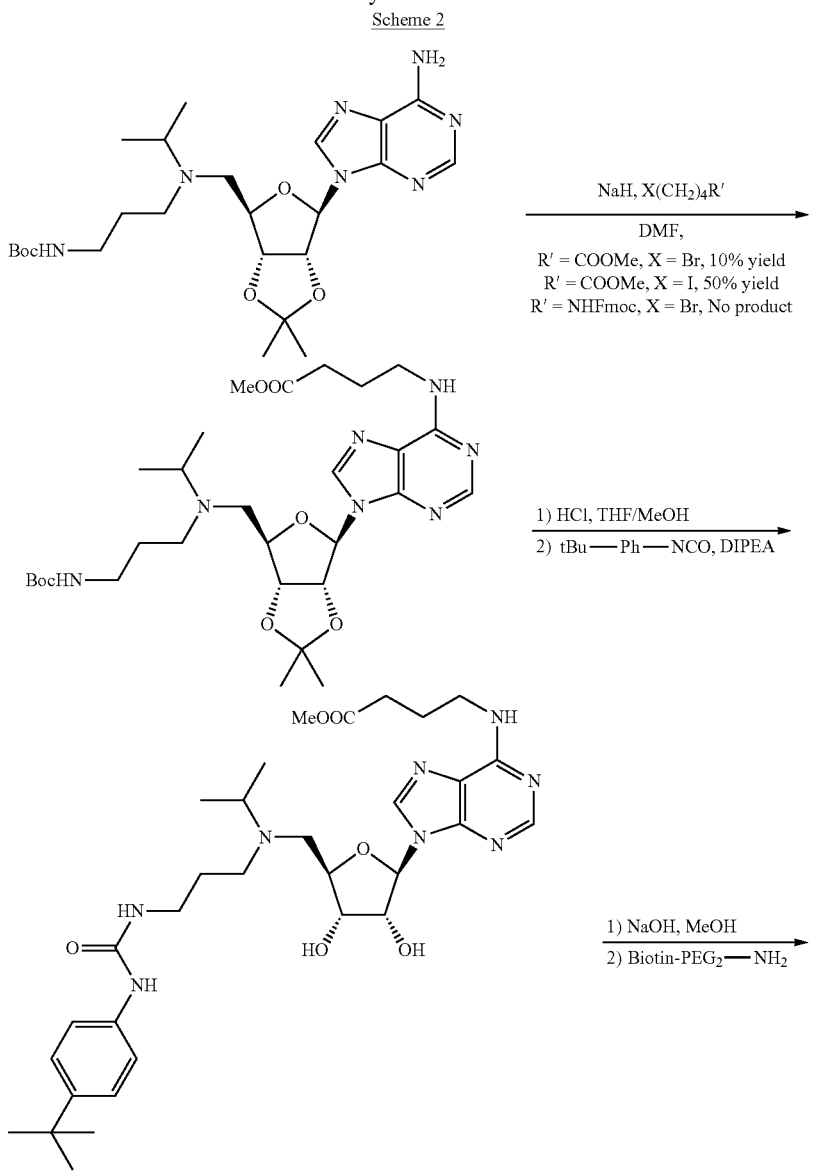

-continued

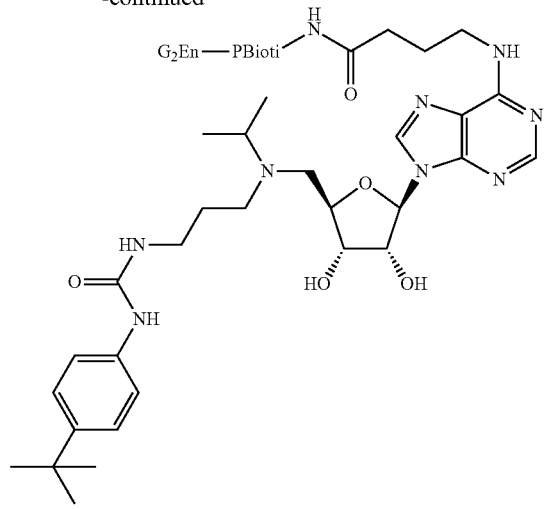

EXAMPLE 1

Fluorescence Polarization Assay

An exemplary protocol for performing a Fluorescence Polarization Assay for detecting the binding of (with or without a test compound) a fluorescence labeled probe to DOT1L, or an analog thereof, is as follows. First, a protein solution comprising DOT1L or an active fragment thereof (e.g., DOT1L SET domain) is prepared in a suitable buffer (e.g., phosphate buffered saline, pH 7.4, 1 mM DTT) is prepared at a desired concentration (e.g., 0.1 μM. 0.5 μM, 1.0 μM, 2.5 μM, 5.0 μM, 10 μM, 20 μM, or 100 μM). Then, a probe solution comprising a compound of formula (I), (Ie), (If) or (Ig) ("FED1-FITC") (depicted below) is prepared.

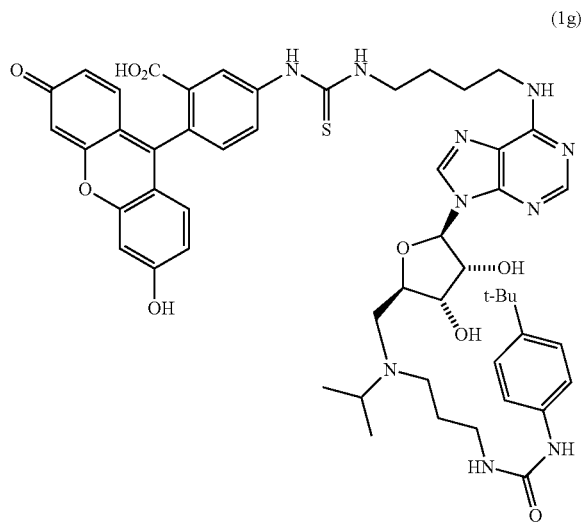 [SMILES: CC(C)N(CCCNC(=O)Nc1ccc(C(C)(C)C)cc1)C[C@H]1O[C@@H](n2cnc3c(NCCCCNC(=S)Nc4ccc(-c5c6ccc(=O)cc-6oc6cc(O)ccc56)c(C(=O)O)c4)ncnc32)[C@H](O)[C@@H]1O]

Exact Mass: 1000.43
Molecular Weight: 1001.16

A volume (e.g., 1 μL, 2.5 μL, 5 μL, 10 μL, 20 μL, 50 μL, or 100 μL) of the protein solution is added to a sample well of a multi-well plate (e.g., a micro titer plate). Then a volume (e.g., 1 μL, 2.5 μL, 5 μL, 10 μL, 20 μL, 50 μL, or 100 μL) of the probe solution is added to each well with or without a test compound. The plate is spun and then incubated at room temperature in the dark for 30 minutes. Binding of the probe to DOT1L or an active fragment thereof is then measured using a fluorometer.

EXAMPLE 2

Differential Scanning Fluorimetry (DFS) Assay

DFS enables assays suitable for high throughput screening assays for the effect of a small molecule on protein stability. DFS assays measures the thermal stability of a target protein and a subsequent increase in protein melting temperature upon binding of a ligand to the protein. Generally, specific binding will stabilize the protein. An exemplary protocol for performing a DFS for detecting the binding of (with or without a test compound) a fluorescence labeled probe to DOT1L, or an analog thereof, is as follows.

First, a protein solution comprising DOT1L or an active fragment thereof (e.g., DOT1L SET domain) is prepared in a suitable buffer at a desired concentration (e.g., 0.1 μM. 0.5 μM, 1.0 μM, 2.5 μM, 5.0 μM, 10 μM, 20 μM, or 100 μM). Then, a probe solution comprising a compound of formula (I), (Ie), (If) or (Ig) is prepared. A volume of the protein solution is combined with a volume of the probe solution in the presence or absence of a test compound. Binding of the probe to DOT1L or an active fragment thereof is then measured using a fluorometer.

The results of one such assay are shown in FIG. 1. The binding effect DMSO, SAH (S-adenosylhomocysteine), EPZ (EPZ004777 reported by Epizyme), JQPROB2B (e.g., a compound of formula (III)), FED1(CP), and FEDPROB) are shown, of which compound of formula (III)) shows reasonable binding affinity against DOT1L.

EXAMPLE 3

Amplified Luminescent Proximity Homogeneous Assay Development

In and ALPHA assay binding of binding partners captured on the beads leads to an energy transfer from one bead to the other, ultimately producing a luminescent signal. Alpha assays require two bead types: donor beads and acceptor beads. Donor beads contain a photosensitizer, phthalocyanine, which converts ambient oxygen to an excited and reactive form of $O_2$, singlet oxygen, upon illumination at 680 nm. Within its 4 μsec half-life, singlet oxygen can diffuse approximately 200 nm in solution. If an Acceptor bead is within that distance, energy is transferred from the singlet oxygen to thioxene derivatives within the Acceptor bead, resulting in light production. If the Donor bead is not in proximity of an Acceptor bead, the singlet oxygen falls to ground state and no signal is produced An ALPHA assay developed based on probes described herein has shown excellent Z' (0.66), and is suitable for high through-put screening. The assay has been used to test the DOT1L inhibitors and the results are in good agreement with DSF assay data. A suitable ALPHA assay can be performed as follows.

Materials:
AlphaScreen Beads (Perkin Elmer #6760619M), Nickel chelate acceptor beads, Streptavidin donor beads, AlphaScreen Plates (Perkin Elmer #6005359), Plate Covers (Costar #6570), Alpha Buffer (50 mM HEPES, 150 mM NaCl, 0.1% w/v BSA, 0.01% w/v Tween20, pH 7.5, Store at 4°, allow to equilibrate to RT before beginning assay).

Two stock solutions (e.g., a protein solution comprising DOT1L or an active fragment thereof and a probe solution comprising a compound of formula (I)) are made at 2× the final concentration in Alpha buffer. The components of these 2× solutions are dependent on the biochemistry of the protein being assayed. All solutions containing Alpha beads should be handled in low light conditions. In general for 384 well assay formats, 10 μL of the protein solution is added to the 384 well alpha plate and the plate is spun at 1000 rpm for 30 s. The plate is incubated at room temperature, then 100 nL of test compounds are pinned into the plate, followed by a second incubation at room temperature. Finally, 10 μL of probe solution is added to the 384 well alpha plate, the plate is spun down and incubated at room temperature and read on a plate reader.

Plate Reader Settings: Plates can be read with an Envision plate reader, which comes with a predefined AlphaScreen program that has the correct excitation and emission wavelengths, cutoff filters, delay time, etc.

ALPHA Assay Specific Protocols:
Alpha Buffer: All reagents were diluted in standard alpha buffer (e.g., 0.5% w/v BSA, 0.05% w/v Tween20, 1 mM DTT added fresh, pH=8.0) and allowed to equilibrate to room temperature prior to addition to plates. After addition of Alpha beads to master solutions all subsequent steps were performed in low light conditions.

A 2× solution of his6-DOT1L+biotinylated probe is made such the final concentration of the components in the final assay volume of 20 μL is: (His6-DOT1L: 80 nM final concentration; Biotin-FED1 (JQ-PROB2B): 40 nM final concentration). 10 μL of this solution is added to the 384 well plate and the plate is spun for 30 s at 1000 rpm 100 nL of experimental compounds in DMSO is added into the 384 well assay plate, and the plate is spun again for 30 s at 1000 rpm. The plates are then incubated at room temperature for 30 minutes.

A 2× solution of alpha beads is made such the concentration of the components in the final assay volume of 20 μL is: (Nickel chelate acceptor bead: 25 μg/mL final concentration; Streptavidin donor bead: 25 μg/mL final concentration). 10 μL of this solution is added to the 384 well plate and the plate is spun for 30 s at 1000 rpm. Plates are incubated at room temperature for 20 minutes, then read on plate reader

What is claimed is:
1. A probe, comprising a compound having formula (I):

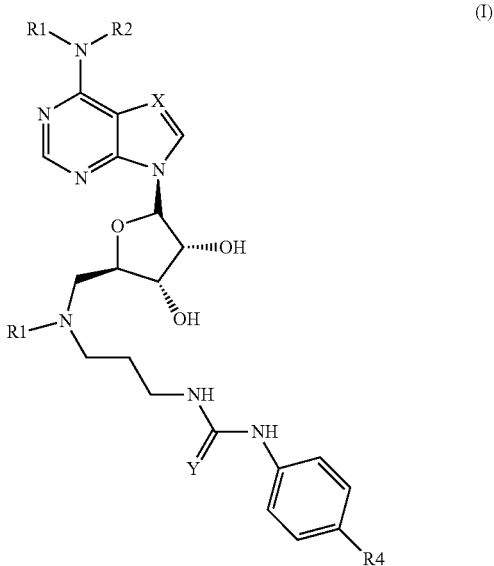

wherein:
X is N or C—R5;
Y is O or S;
R1 is hydrogen or $C_{1-3}$ alkyl;
R2 is hydrogen, $C_{1-3}$ alkyl, or R6;
R3 is hydrogen, $C_{1-6}$ alkyl, or R6;
R4 is $C_{1-8}$ alkyl, or N(R6)(R7), provided that one of R2, R3, and R4 is, or includes, R6;
R5 is hydrogen, halo, $C_{1-6}$ alkyl, or $C_{1-6}$ haloalkyl;
R6 is Z—R8;
Z is a divalent group consisting of any 1, 2, 3, 4, or 5 of the following independently selected moieties:
(i) $C_{1-30}$ alkylene;
(ii) heteroalkylene that spans from 3-20 atoms in length wherein from 1-8 of the atoms in the span are heteroatomic groups that are each independently selected from N, NH, N—$C_1$-$C_6$ alkyl, O, and S, provided that there is at least one carbon atom between the occurrence of any two heteroatomic groups;
(iii) polyheteroalkylene chain that spans from 21-100 atoms in length wherein from 1-50 of the atoms in the span are heteroatomic groups that are each independently selected from N, NH, N—$C_1$-$C_6$ alkyl, O, and S, provided that there is at least one carbon atom between the occurrence of any two heteroatomic groups;
(iv) $C_{2-30}$ alkenylene chain; and
(v) —OC(=O)—, —C(=O)O—, —NHC(=O)—, —C(=O)NH—, —NHC(=O)NH—, —NHC(=S)NH—, —OC(=O)NH—, and —NHC(=O)O—;
R7 is hydrogen or $C_{1-3}$ alkyl; and
R8 is an affinity tag or a fluorescent label.
2. The probe of claim 1, wherein R2 is R6.
3. The probe of claim 1, wherein R3 is R6.
4. The probe of claim 1, wherein R4 is N(R6)(R7).

5. The probe according to claim 1, wherein R8 is an affinity tag.

6. The probe according to claim 1, wherein R8 has an affinity for streptavidin.

7. The probe according to claim 1, wherein R8 has formula (II):

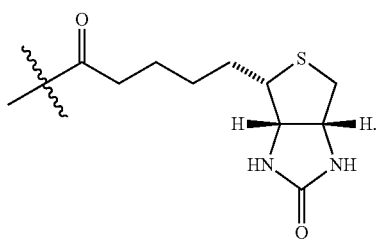

8. The probe according to claim 1, wherein R8 is a fluorescent label.

9. The probe of claim 4, wherein R8 is FITC.

10. The probe according to claim 1, wherein Z is a divalent group consisting of one, two, three, four, or five groups independently selected from the group consisting of $C_{1-30}$ alkylenes; a heteroalkylene or polyheteroalkylene; —NHC(=O)—, —C(=O)NH—, and —NHC(=S)NH—.

11. The probe of claim 10, wherein the polyheteroalkylene is (PEG)n, wherein PEG represents a polyethylene glycol, and n is an integer from 2-27.

12. The probe according to claim 1, wherein R3 is $C_{1-6}$ alkyl.

13. The probe according to claim 1, wherein R4 is $C_{1-8}$ alkyl.

14. The probe according to claim 1, wherein R2 is hydrogen.

15. The probe of claim 1, wherein the compound is selected from the group consisting of:

formula (III)

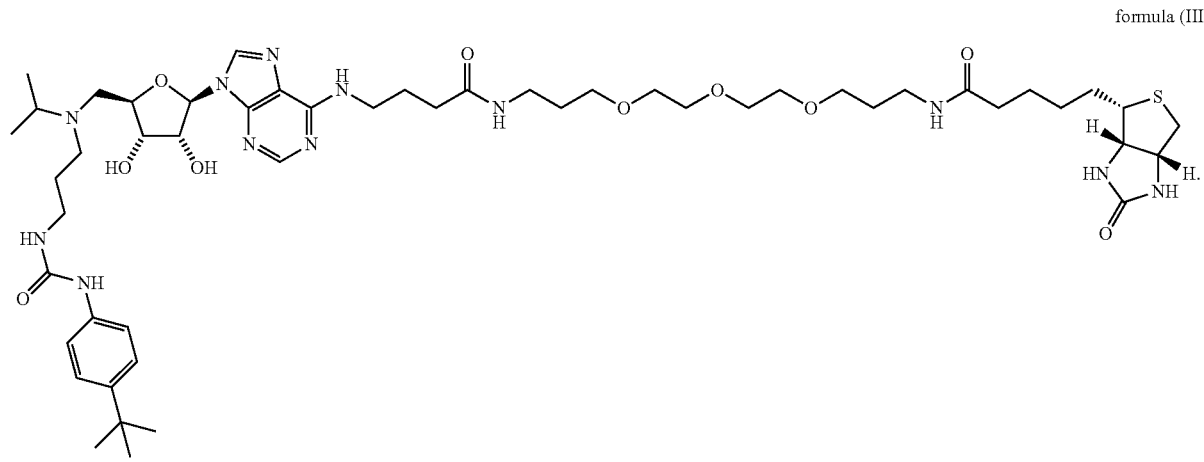

formula (IV)

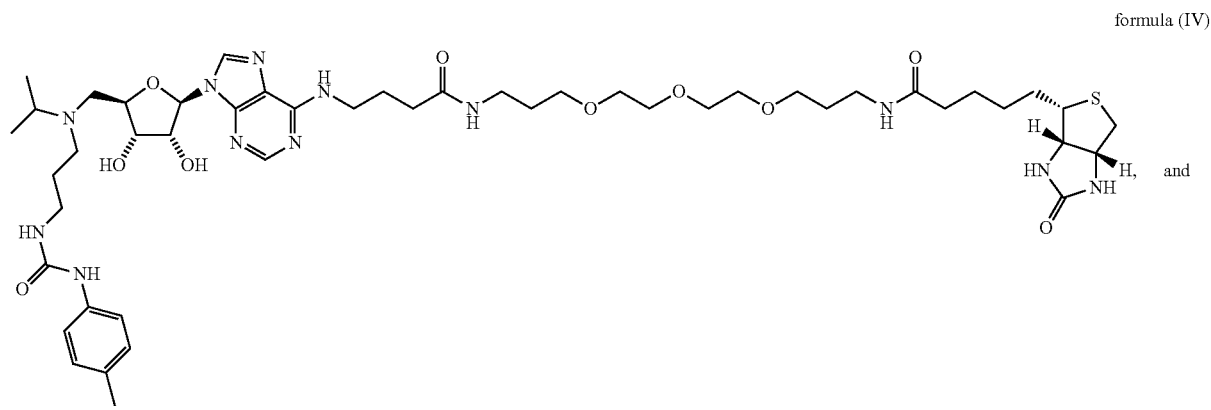

and

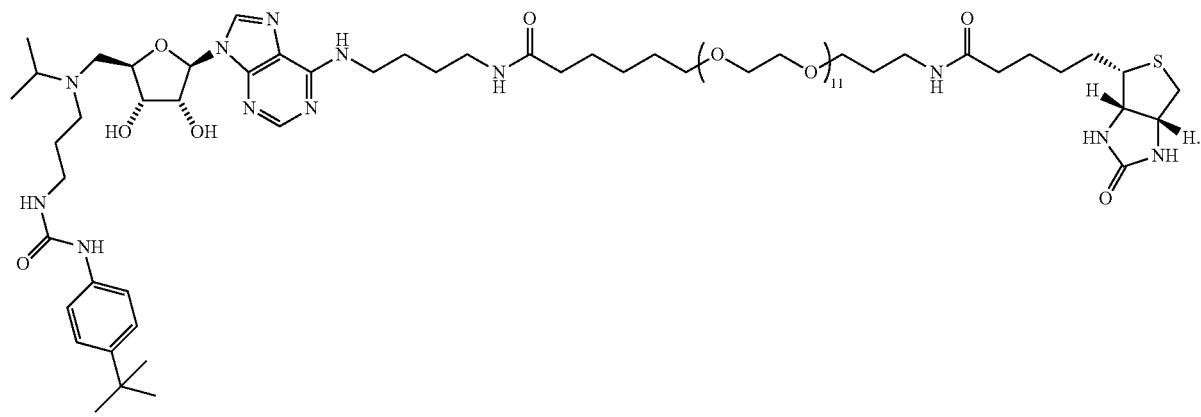
formula (V)
16. The probe according to claim 1, wherein the probe further comprises a solid support.
17. The probe of claim 16, wherein the solid support is a bead.
18. The probe of claim 17, wherein the bead is coated with a protein.
19. The probe of claim 18, wherein the protein is streptavidin.
20. The probe of claim 1, wherein the compound is selected from the group consisting of:
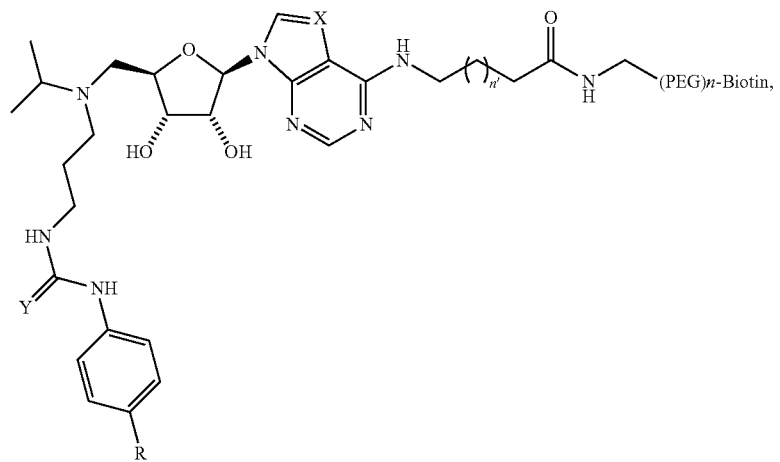
(Ia)
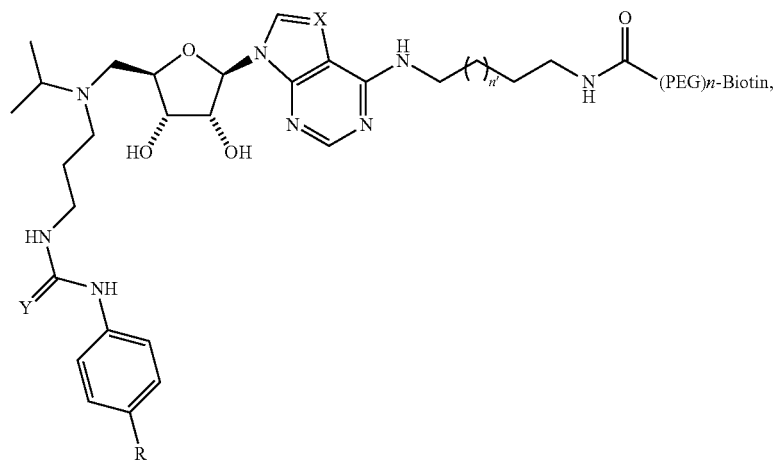
(Ib)

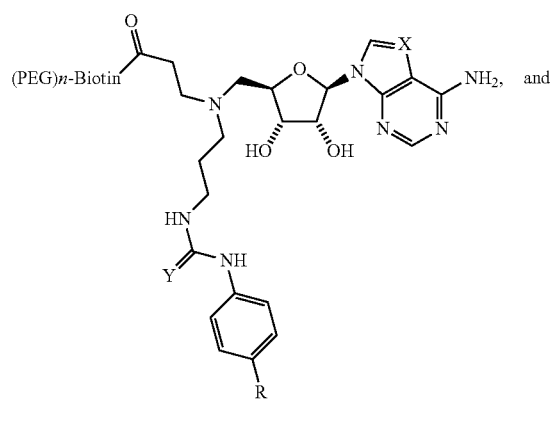
(Ic)
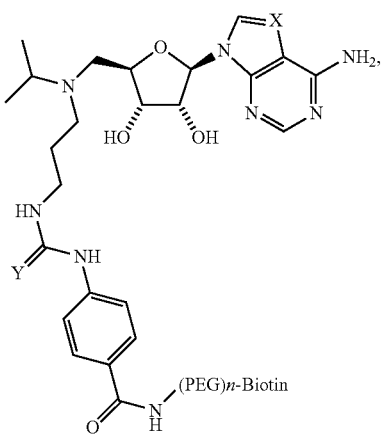
(Id)
wherein:
n is 2-27;
n' is 0-10;
X is N, CH, C—Cl, C—CH$_3$, or C—CF$_3$;
Y is O or S; and
R is t-butyl or methyl.
21. The probe of claim 1, wherein the compound is selected from the group consisting of:
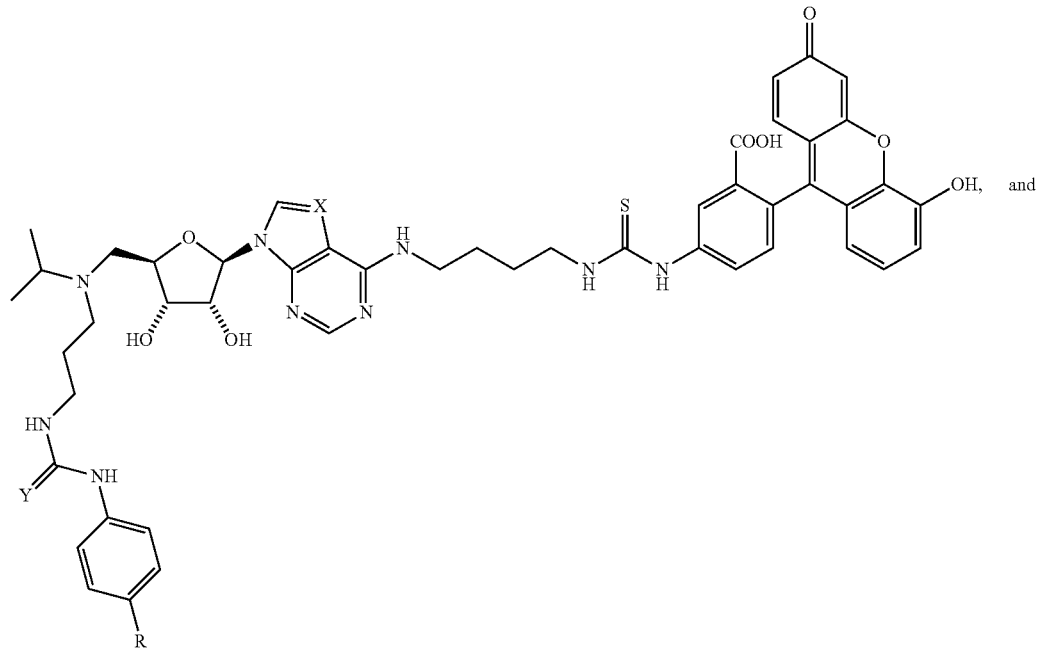
(Ie)

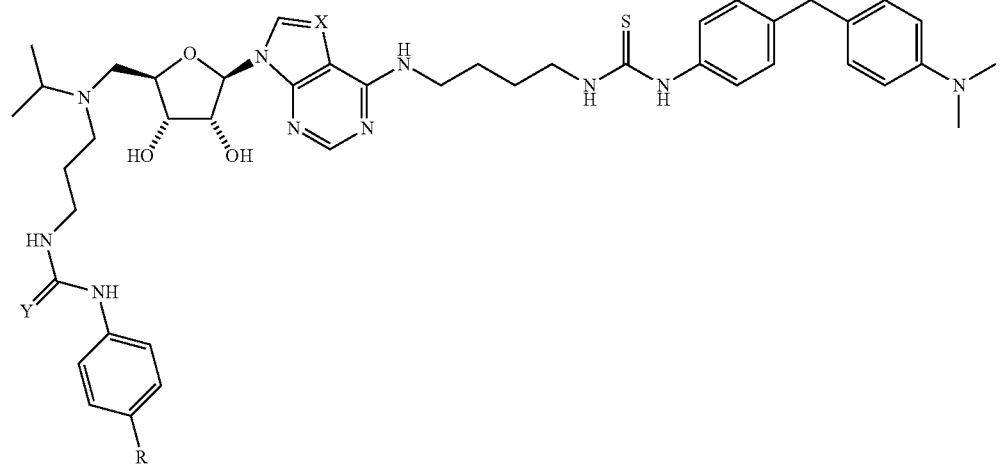
wherein:
  X is N or C—R5;
  R5 is hydrogen, halo, $C_{1-6}$ alkyl, or $C_{1-6}$ haloalkyl;
  Y is O or S; and
  R is t-butyl or methyl.
* * * * *

UNITED STATES PATENT AND TRADEMARK OFFICE
CERTIFICATE OF CORRECTION

PATENT NO. : 9,535,067 B2  
APPLICATION NO. : 14/904572  
DATED : January 3, 2017  
INVENTOR(S) : James E. Bradner, Alexander Federation and Jun Qi Page 1 of 2

It is certified that error appears in the above-identified patent and that said Letters Patent is hereby corrected as shown below:

On the Title Page

Item (57):
Line 2 of the ABSTRACT, after the word 'transferase', delete "(DOTIL)" and insert -- (DOT1L) -- therefor.

Item (57):
Line 4 of the ABSTRACT, after the word 'of', delete "DOTIL" and insert -- DOT1L -- therefor.

Item (57):
Line 4 of the ABSTRACT, after the words 'inhibitors of', delete "DOTIL" and insert -- DOT1L -- therefor.

Item (57):
Line 6 of the ABSTRACT, after the words 'activity of', delete "DOTIL" and insert -- DOT1L -- therefor.

Item (57):
Line 6 of the ABSTRACT, after the words 'inhibitors of', delete "DOTIL" and insert -- DOT1L -- therefor.

Signed and Sealed this  
Twenty-eighth Day of March, 2017

Michelle K. Lee  
*Director of the United States Patent and Trademark Office*

CERTIFICATE OF CORRECTION (continued)

In the Claims

Column 18:

In Claim 1, delete " 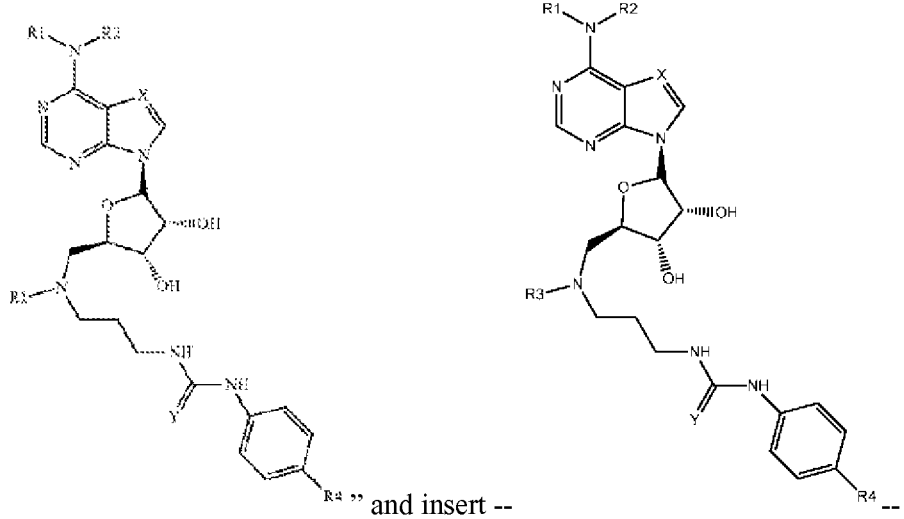 " and insert -- -- therefor.

Column 19-20:
In Claim 15, delete

"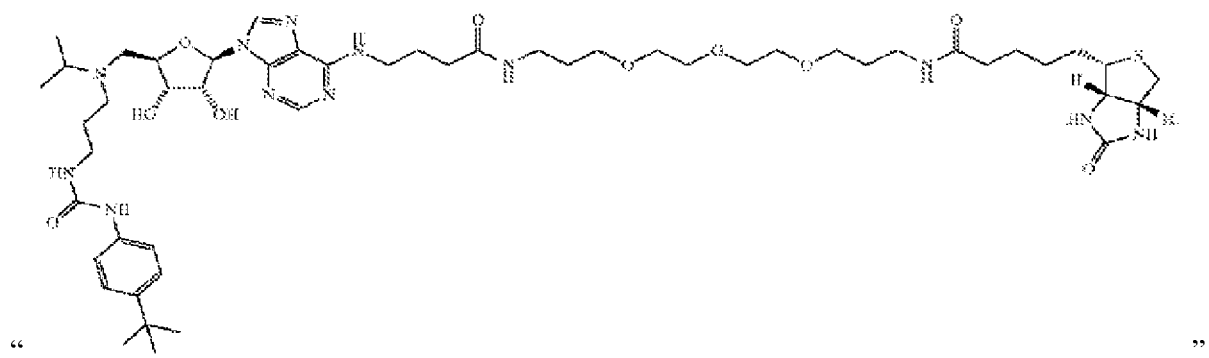"

and insert

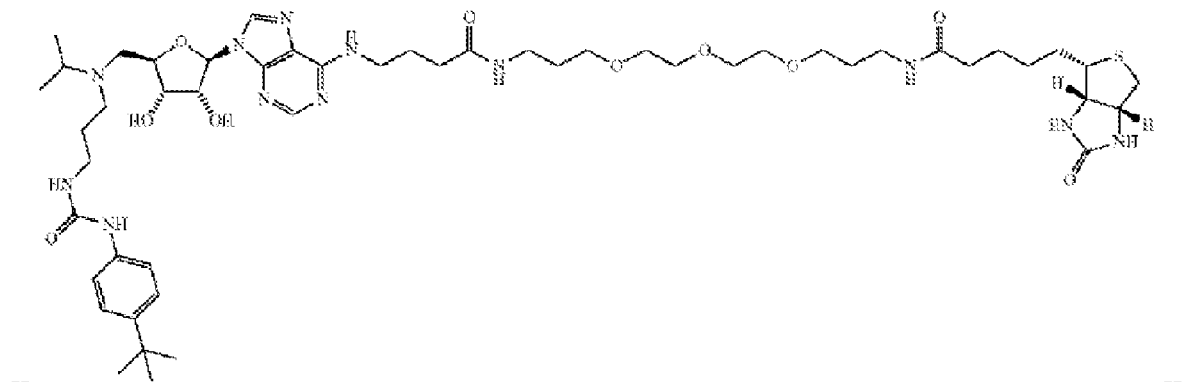

-- -- therefor.